US00PP28415P2

(12) United States Plant Patent
Fang

(10) Patent No.: US PP28,415 P2
(45) Date of Patent: Sep. 19, 2017

(54) ***ONCOSTELE* HILO FIRECRACKER 'NEW YEAR' PLANT**

(50) Latin Name: *Oncostele*
Varietal Denomination: New Year

(71) Applicant: James Yen Jen Fang, Mountain View, HI (US)

(72) Inventor: James Yen Jen Fang, Mountain View, HI (US)

(73) Assignee: James Yen Jen Fang, Mountain View, HI (US)

( * ) Notice: Subject to any disclaimer, the term of this patent is extended or adjusted under 35 U.S.C. 154(b) by 0 days.

(21) Appl. No.: 14/998,915

(22) Filed: Mar. 4, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Annette Para

(57) ABSTRACT

A new variety of orchid plant of the genus *Oncostele*, named *Oncostele* Hilo Firecracker 'New Year', distinguished particularly by flowers of a clean and striking color of medium size that are arranged pleasingly on a raceme and growing quickly to sexual maturity.

2 Drawing Sheets

Latin name of the species and grex of the plant claimed: The Latin name of the species and grex of the plant claimed is *Oncostele* Hilo Firecracker.

Variety denomination: The present invention comprises a new and distinct cultivar of *Oncostele* orchid and hereinafter referred to by the name *Oncostele* Hilo Firecracker 'New Year'.

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The genus *Oncostele* is an artificial intergeneric hybrid of orchids between three genera in the subtribe Oncidiinae; *Miltonia, Odontoglossum* and *Oncidium.*

The first *Oncostele* hybrid was created in 1901 by a Mr. Henri Graire of Amiens, France and registered by the same. Due to the varying percentages of the parent genera that make up *Oncostele* and the gene expression in their progeny, *Oncostele* varies in morphology and size. All exhibit a sympodial growth habit. There are now 552 distinct *Oncostele* hybrids as of December 2015.

*Oncostele* hybridizing is accomplished through sexual methods. Asexual propagation of *Oncostele* is done in aseptic tissue culture from apical or axillary shoots.

The new cultivar was discovered within a group of sexually produced plants on Jul. 8, 2009. The inventor selected *Oncostele* Hilo Firecracker 'New Year' from a population of 220 plants grown in 3.25 inch square black plastic pots, grown in a poly-film covered greenhouse in Mountain View, Hi. *Oncostele* Hilo Firecracker 'New Year' was re-flowered and submitted by the inventor to a commercial tissue culture laboratory in Bangkok, Thailand on May 7, 2012 for asexual reproduction via tissue culture technique.

Other seedlings of the same varieties that were used to produce *Oncostele* Hilo Firecracker 'New Year' have been commercially available from others.

The characteristics of *Oncostele* Hilo Firecracker 'New Year' as described herein have demonstrated to be fixed and retained through successive generations of asexual reproduction. *Oncostele* Hilo Firecracker 'New Year' reproduces true to type. The characteristics are clearly distinguishable from the characteristics of those other plants. The inventor has reason to believe that *Oncostele* Hilo Firecracker 'New Year' is superior to other seedlings in flower color.

BRIEF SUMMARY OF THE INVENTION

The following traits have been repeatedly observed and are determined to be basic characteristics of the new cultivar which in combination distinguish this *Oncostele* orchid as a new and distinct cultivar:

Flowers of the new cultivar are dark red in color with dark red sepals and petals. The labellum is red centrally with glossy, dark orange mid-lobes extending inwards horizontally, lower half cream overlaid with irregular dark orange spotting. The callus is matte orange and develops as a swelling in the lip terminating into many small diverging horns divided by a central crest about 0.5 centimeters (cm) long. The anther cap is light yellow in color. The column is red overlaid orange terminally. The column wings are undulating, rectangular and orange in color. The flowers are rigid and bear no fragrance.

The natural horizontal spread is 6.7 cm; natural vertical spread is 6.4 cm; dorsal sepal width 1.6 cm; dorsal sepal length 3.3 cm; petal width 1.4 cm; petal length 3.0 cm; lateral sepal width 1.3 cm; lateral sepal length 3.0 cm; labellum width 2.9 cm; labellum length 2.7 cm.

The plant produces one branching inflorescence on first bloom with 35 flowers.

Inflorescence is a basal raceme, upright or arching, branching and approximately 65 cm long. The plant is relatively compact and the size of the inflorescence is appropriate to the overall size of the plant and typical pot size for this cultivar.

There are generally six leaves per mature psuedobulb: two from the apex and four from the base. The apical leaves measure 35 cm long and are 5 cm wide. The leaves from the base of the psuedobulb measure 15-20 cm long and are 5 cm wide. Axillary leaves, or bracts, are not common below the leaves at the base of the psuedobulb.

The shape of the leaf is lanceolate acuminate and they are semi-conduplicate at the base. The texture and substance is slightly undulate and somewhat coriaceous. The plants of *Oncostele* Hilo Firecracker 'New Year' grow to maturity and flower in approximately 18 months.

Plants of the new cultivar have not been observed under all possible environmental conditions. The phenotype may vary significantly with variations in the environment, such as temperature, light intensity, and day length, without any change in genotype.

The instant plant differs from parent cultivars in flower color. The closest comparison to the new cultivar can be made to the parent cultivars used to create *Oncostele* Hilo Firecracker 'New Year'. The original unpatented plant material; named *Oncostele* Catatante 'Pacific Sun Spots' and *Oncostele* Aloha Sparks 'Pele's Glow' possess the same growth habit and speed to maturation, but lack the unique, attractively large dark red flowers of *Oncostele* Hilo Firecracker 'New Year'.

BRIEF DESCRIPTION OF THE DRAWINGS

The drawings show the colors of the new variety as nearly true as possible with an illustration of this type. In the drawings:

The drawing on the first sheet is a single plant to illustrate growth habit and general characteristics typical of this new cultivar.

Figure 1:
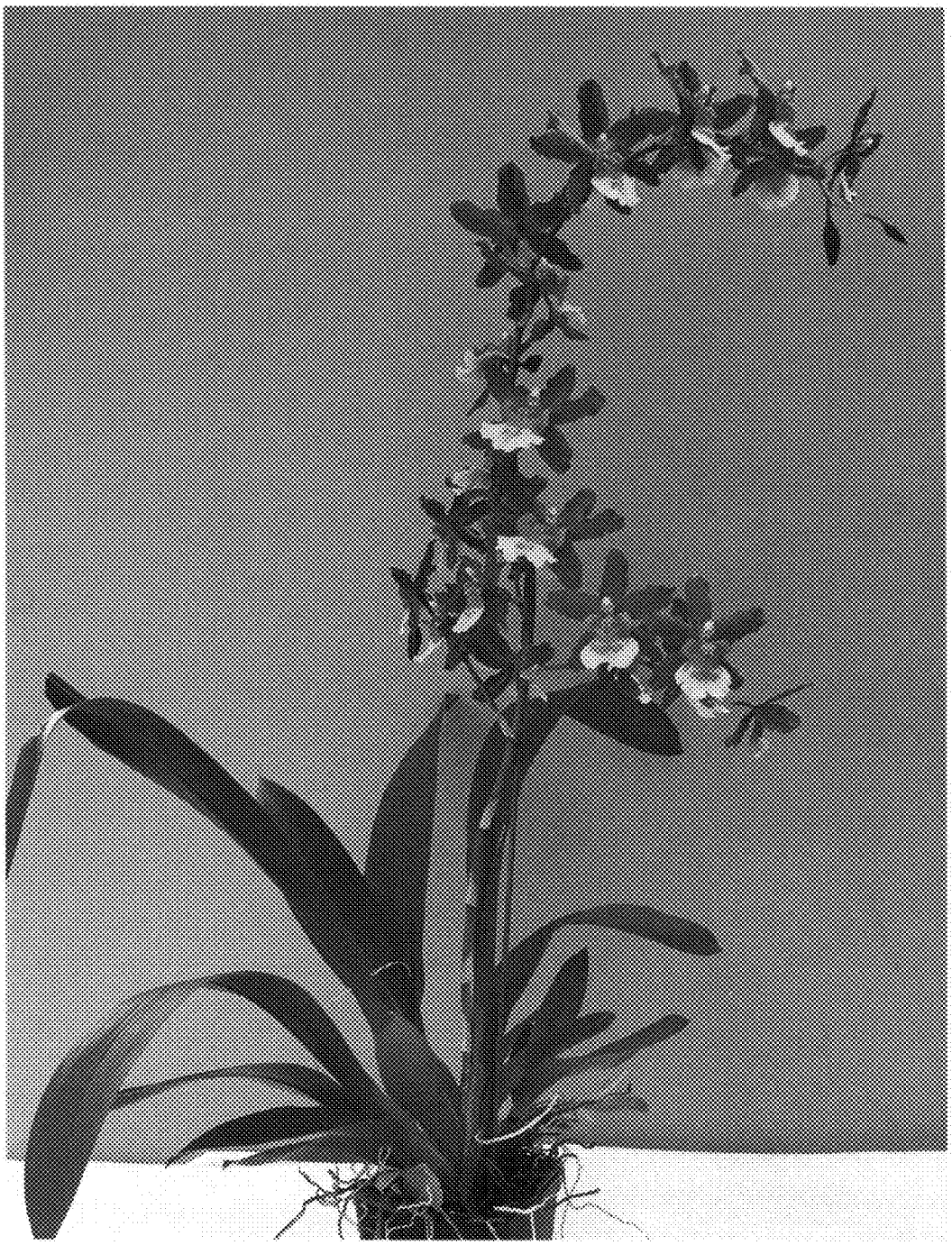
Figure 2:
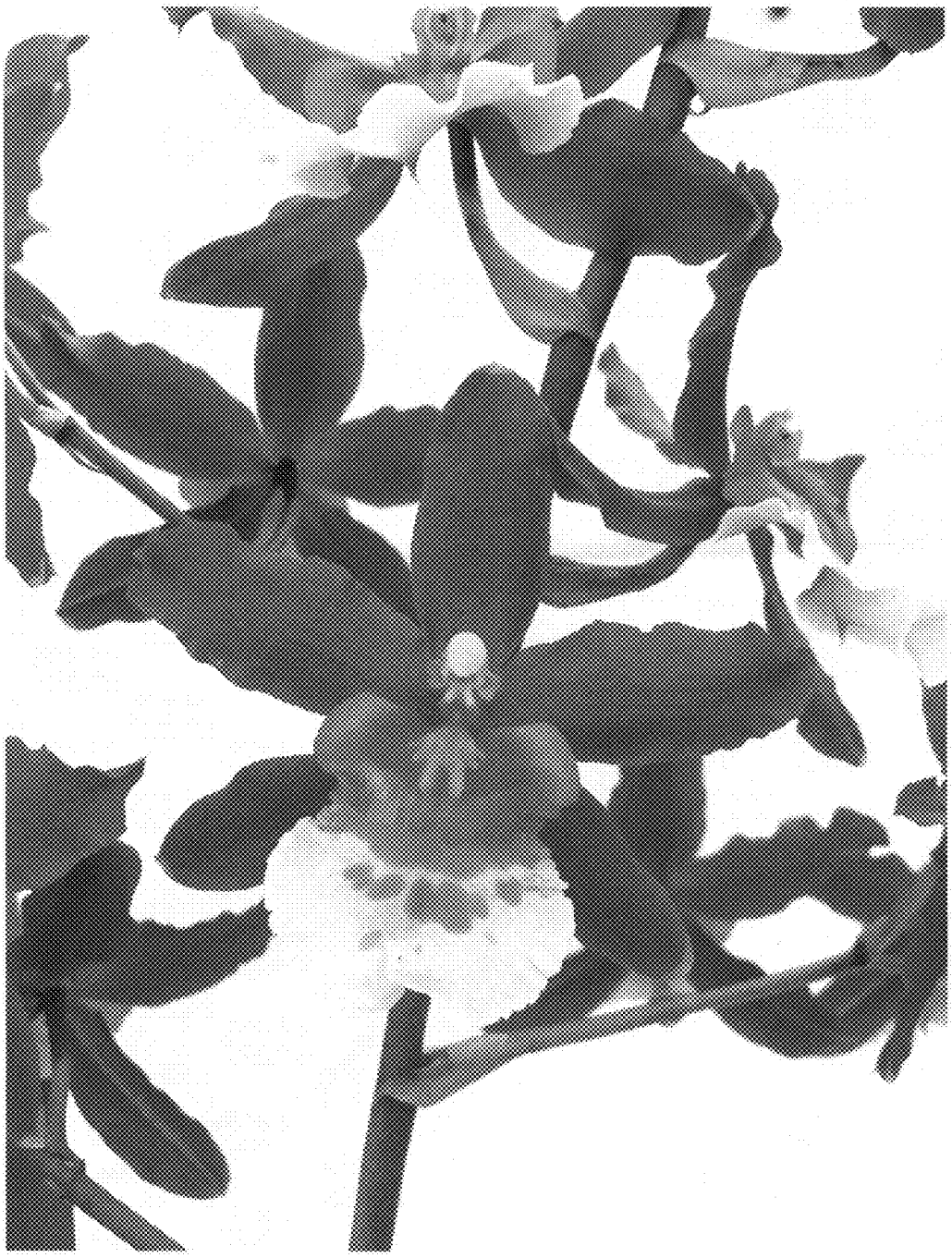

The drawing on the second sheet is a single flower of *Oncostele* Hilo Firecracker 'New Year' to illustrate shape and color.

DETAILED BOTANICAL DESCRIPTION

All color references are measured against the Pantone® Color System. Colors and numerical measurements are approximate, as plant growth and development depend on environmental conditions and cultural practices such as: light levels, temperature, water quality, fertilization formula and rate, among others, without however, any variance in genotype.

Plants used for this description are 18 months old in vivo and grown in 3.25 inch square, black plastic pots, grown in a poly-film covered greenhouse in Mountain View, Hi. Day temperatures range from 75-85° F. and night temperatures range from 55-65° F. Light levels are approximately 2500 foot candles. This information reflects the annual variations for the area.

Botanical classification: *Oncostele* Hilo Firecracker 'New Year'.

Parentage: Seedling selected from the cross of the following.

*Seed parent.*—*Oncostele* Catatante 'Pacific Sun Spots'.

*Pollen parent.*—*Oncostele* Aloha Sparks 'Pele's Glow'. The designations above list the Genus and grex for both parents.

Propagation:

*Type.*—Asexual propagation by aseptic tissue culture through Axillary shoot.

*Time to initiate and elongate roots in-vivo.*—Approximately 90 days.

*Time to produce fully rooted young plant.*—Approximately 250 days.

Root description: Velamen covered roots, approximately 0.2 cm in diameter, and white in color with yellow/green growing tip. The exact shades of white and yellow/green vary greatly with minimal changes to environmental conditions.

Plant description: Under optimal growing conditions, plants of the new cultivar attain a mature size of about 28 cm (top of leaf plane) and 4 cm wide (width of largest psuedobulb).

Foliage description:

*Arrangement.*—Sympodial growth habit.

*Quantity of leaves per growth.*—Each sympodial growth has shown six leaves, two on the apex of the psuedobulb and four from the axis at the base.

*Leaf length.*—Leaves measure up to 35 cm in length.

*Leaf width.*—The width of the largest leaf measures 5 cm.

*Leaf shape.*—The shape is lanceolate acuminate from base to tip, texture and substance is slightly undulate and somewhat coriaceous throughout.

*Leaf apex (observed).*—The apex measures approximately 28 cm.

*Psuedobulb shape.*—The psuedobulb shape is a laterally compressed ovoid.

*Psuedobulb length.*—The psuedobulb is approximately 9-12 cm long.

*Psuedobulb width.*—The psuedobulb is approximately 4 cm wide and 3 cm thick.

*Foliage color.*—Under the described growing conditions, the foliage color on both sides of the leaves is similar to Pantone® 7483C (green). There is no vein color distinction. The psuedobulb color is similar to Pantone® 378C (green).

Flower/inflorescence description:

*Description.*—Upright or arching raceme similar in color to Pantone® 378C (green) approximately 0.3-0.5 cm in diameter, coriaceous, branching, approx. 65.0 cm long on a first bloom plant with 35 flowers. Each internode is coriaceous in texture, carrying 4-6 flowers spaced 2.0-3.0 cm apart and varying between 9.0-12.0 cm in length. Buds are ovoid, 0.6-0.8 cm in diameter and 2.5-2.8 cm in length. Bud coloration is unique to each individual flower, being different shades of red as the bud matures. As such, selecting an individual color from a color chart would be both difficult and misleading. Pedicels are coriaceous in texture, approximately 0.1 cm in diameter and 0.4 cm in length. Flowers begin approximately ⅔ of the way up the raceme and are spaced 2.0-3.0 cm apart. The size of the inflorescence is appropriate to the overall size of the plant and typical pot size of the cultivar.

*Dimensions.*—Flower dimensions are: natural horizontal spread is 6.7 cm; natural vertical spread is 6.4 cm; dorsal sepal width 1.6 cm; dorsal sepal length 3.3 cm; petal width 1.4 cm; petal length 3.0 cm; lateral sepal width 1.3 cm; lateral sepal length 3.0 cm; labellum width 2.9 cm; labellum length 2.7 cm.

*Coloration*.—The dominant flower color that appears on the sepals, petals and upper half of the labellum is a dark red, similar to Pantone® 7624C. The sepals and petals are dark red; similar to Pantone® 7624C. The upper half of the labellum is dark red; similar to Pantone® 7624C. The mid-lobes are orange; Pantone® 159C, extending inward horizontally. The lower half of the labellum is cream; similar to Pantone® 7604C, overlaid irregular orange spotting; Pantone® 159C. The orange extending outward from the callus is Pantone® 159C. The anther cap is bright yellow; Pantone® 101C. The base color of the column is red; similar to Pantone® 7624C, overlaid orange Pantone® 159C terminally. The pollinia are completely concealed by the anther cap. If this is removed, the pollinia may be extracted. The pollinia are deep yellow; Pantone® 143C, but range in shades of yellow as the flower ages.

Quantity of flowers & time to flower:

*Flower longevity*.—Flowers can last longer than 6 weeks on the plant with good environmental conditions. A first bloom plant will produce about 35 flowers depending on environmental conditions.

*Time to flower*.—From fully rooted tissue culture plants is approximately 18 months.

*Natural flowering season*.—This plant has appeared to be free flowering.

*Fragrance*.—No fragrance has been detected.

*Reproductive organs*.—The Stamens, style and stigmas are fused into a short structure called the column, possessing one terminal anther with pollen grains united to pollinia, which are covered by an anther cap. The stigma is located under the column behind the pollinia. The ovary is inferior, with three carpels being present.

*Column*.—The column is erect with rectangular wings on either side of the stigma, 0.4 cm wide by 0.8 cm long.

*Pollinia*.—Two oval masses of pollen are present, about 0.15 cm in diameter and 0.1 cm long.

*Stigma*.—The stigma is concave, round, very glossy and sticky.

*Ovary*.—The ovary is about 2.0 cm long by 0.2 cm wide.

*Seed*.—Seed production has not been observed.

Disease & pest resistance: Resistance or susceptibility to know pathogens and pests of *Oncostele* have not been observed on plants grown under commercial production conditions.

Hardiness zone: The type plant of *Oncostele* Hilo Firecracker 'New Year' was commercially grown in Mountain View, Hi. — USDA Hardiness Zone 11. Data from other plants of *Oncostele* Hilo Firecracker 'New Year' in other USDA Hardiness zones is currently unavailable.

General observations: Plants of *Oncostele* Hilo Firecracker 'New Year' produce a pleasing arrangement of medium sized, dark red, star shaped flowers with a clean, striking color on a branching raceme that is desirable in proportion for the size of the plant. The flowers are long lasting and pleasantly shaped. The plant grows quickly to sexual maturity.

What is claimed is:

1. A new and distinct variety of orchid plant named *Oncostele* Hilo Firecracker 'New Year' substantially as illustrated and described herein.

* * * * *